(12) United States Patent
Tsubooka et al.

(10) Patent No.: US 6,460,196 B2
(45) Date of Patent: Oct. 8, 2002

(54) GOGGLES HAVING V-SHAPED ELASTIC COUPLING MEMBER

(75) Inventors: Toru Tsubooka, Sakurai; Makoto Shinya, Higashiosaka, both of (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 0 days.

(21) Appl. No.: 09/928,629

(22) Filed: Aug. 13, 2001

(65) Prior Publication Data

US 2002/0020005 A1 Feb. 21, 2002

(30) Foreign Application Priority Data

Aug. 11, 2000 (JP) ........................................ 2000-244550

(51) Int. Cl.⁷ .................................................. A61F 9/02
(52) U.S. Cl. .............................................. 2/428; 2/452
(58) Field of Search .......................... 2/452, 428, 430, 2/426, 440, 439

(56) References Cited

U.S. PATENT DOCUMENTS

| 5,617,589 A | * | 4/1997 | Lacore et al. | 2/452 |
| 6,047,410 A | * | 4/2000 | Dondero | 2/426 |
| 6,317,897 B1 | * | 11/2001 | Chiang | 2/428 |

* cited by examiner

Primary Examiner—Peter Nerbun
(74) Attorney, Agent, or Firm—Koda & Androlia

(57) ABSTRACT

Goggles include an eye-cup and a belt that are coupled by means of a coupling member. The eye-cup and the coupling member can be engaged and disengaged easier compared with conventional goggles. In the goggles, at a connecting end of the coupling member is provided an elastic bent piece with a V-shape section and a spring property. And a connection recess is provided on the eye-cup. The elastic bent piece of the coupling member and the connection recess of the eye-cup are fixed together in a mutual engaging state. The engaging state can be released by narrowing the gap distance in the V-shape of the elastic bent piece.

7 Claims, 6 Drawing Sheets

GOGGLES HAVING V-SHAPED ELASTIC COUPLING MEMBER

FIELD OF THE INVENTION

The present invention relates to goggles, more particularly relates to goggles suitably used for swimming and the like.

PRIOR ART

Conventional Goggles preferably used for swimming and the like are shown in FIG. 6. This type of goggles has eye-cups 21 for protecting the eyes of a wearer and an expandable belt 22 for being fit with the head of the wearer and they are connected by means of coupling members 23 provided on both of the end of the belt. The eye cup herein means a cup shaped member for protecting an eye of a wearer that is a composing part of goggles.

In a coupling state of the conventional goggles, an elastic piece 24 provided on the coupling member comes out through a fitting aperture 25 provide on the eye-cup 21. When separating the eye-cup 21 and the coupling member 23, the elastic piece 24 of the coupling member 23 is pushed down in the fitting aperture 25, and, with this state, is pulled in the separation direction so as to be released from the fitting apertures 25 of the eye cup 21.

However, such separation with the elastic piece 24 of the coupling member 23 being pushed down and pulled in the separation direction is not easy, and the separation and coupling between the members are rather troublesome.

SUMMARY OF THE INVENTION

It is, therefore, an object of the present invention to provide goggles in which an eye-cup and a coupling member can be easily and reliably connected and separated.

In order to achieve the above object, the present invention has the following technical features.

(1) Goggles according to the present invention include an eye-cup and a belt member which are connected by means of a coupling member. On a connecting end for the coupling member is provided with an elastic bent piece which has a V-shape section and a spring property. The eye-cup is provided with a connection recess. The elastic bent piece of the coupling member and the connection recess of the eye-cup are fixed in a mutual engaging state. This engaging state can be released by narrowing the gap distance of the V-shape.

In the goggles, the elastic bent piece of the coupling member, which has a V-shape section and a spring property, and the connection recess of the eye-cup are engaged mutually fixed. When the gap in the V-shape is narrowed, the mutual engagement can be released.

(2) The bent portion of the elastic bent piece having a V-shape section may be formed with a cut for adjusting the strength of the spring property.

When the length or the cut is made long in this construction, the spring property may be set flexible, while when short, the spring property may be set stiff.

(3), The cut formed on the bent portion may be formed with an oblong aperture.

With the cut being made in an oblong aperture, the surrounding area is connecting in a loop fashion and this gives anti-breakableness against repetitious use.

(4), In order for the elastic bent piece and the connection recess to be engaged each other, a pair of engaging protrusion and dent may be formed.

The pair of engaging protrusion and dent may be formed at least one of an upper face and a lower face of the elastic bent piece and the connection recess. And the engaging protrusion and dent may be either on the connection recess or the bent elastic piece.

(5) The engaging protrusion and the associated engaging dent, or the pair of engaging protrusion and dent, may be formed to prevent an unwanted removal of the eye-cup from the coupling member contrary to a wearer's intention.

For this purpose, for example, the engaging protrusion and the associated engaging dent may be formed oblong transversely with the separation direction of the connecting members.

(6) The engaging protrusion and the associated engaging dent may be formed to prevent displacement and/or mutual rotating movement between the eye-cup and the coupling member.

For this purpose, for example, the engaging protrusion and the associated engaging dent may for formed oblong along with the separation direction of the coupling members.

(7) The eye-cup has a lens member and an elastic face abutting member and these members may be integrally fixed together.

With this construction, the lens member and the elastic face abutting member are handled as one body eye-cup. Methods of the fixing them together include, for example, weld.

DESCRIPTION OF THE PREFERRED EMBODIMENTS OF THE INVENTION

Figure 1:
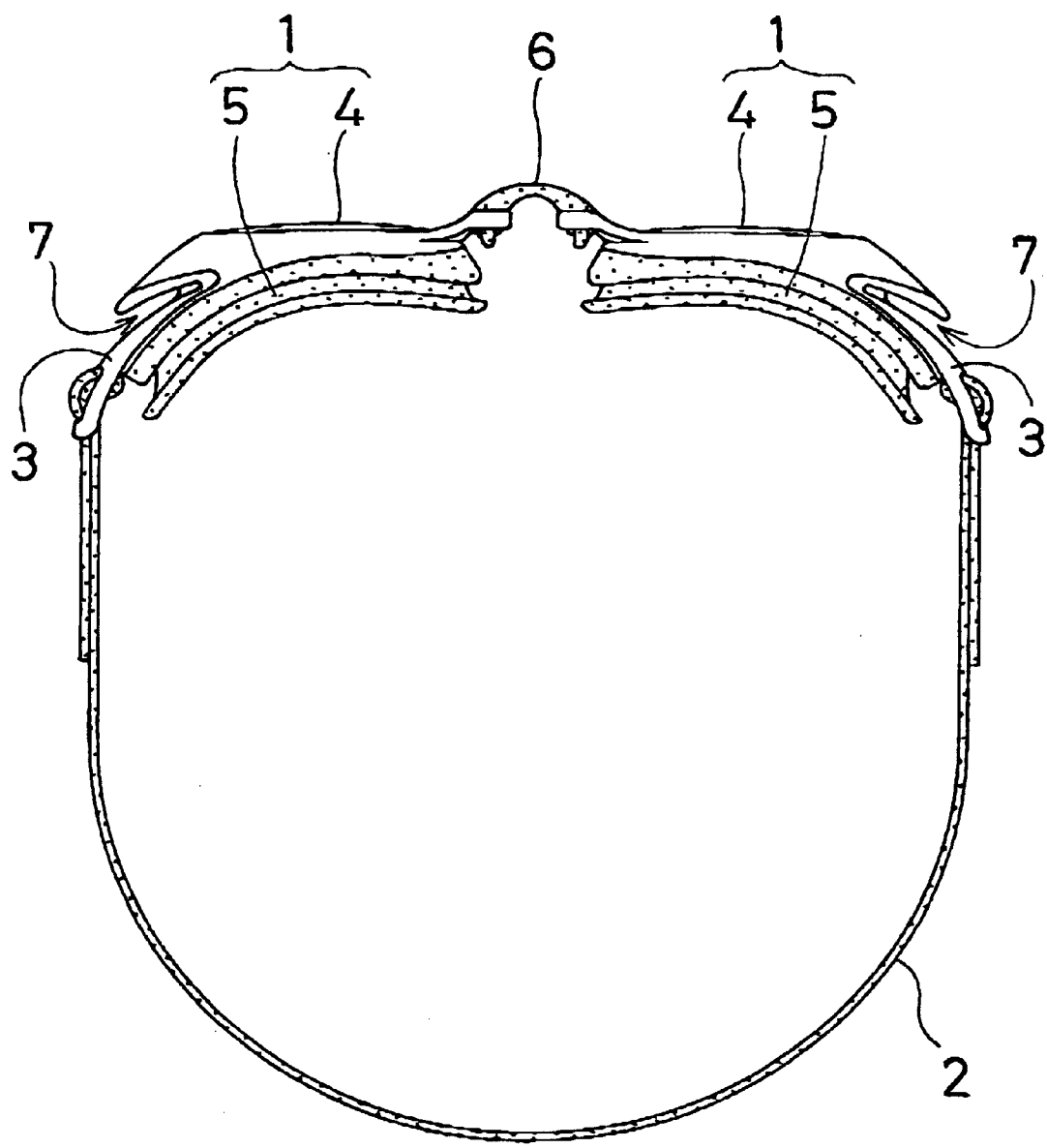
FIG. 1 is a plane view of goggles in one embodiment of the present invention.

As shown in FIGS. 1 to 5, goggles of one embodiment are designed for swimming. The goggles have eye-cups 1 for protecting the eyes of a wearer from water, an elastic belt 2 (made of elastomer) for being fit on the head of the wearer, and coupling members 3 (made of poly-carbonate) provided on the both sides for coupling the eye-cups 1 and the belt 2 together.

Each of the eye-cups 1 includes a lens member 4 (made of polycarbonate) and an elastic face-abutting member 5 (made of elastomer). They are integrally welded together. In a store of sporting goods and the like, in case a purchaser for goggles has eyes with different eye-sights, it may be necessary to fix goggles with lenses of different degrees for respective eyes. In this embodiment, the lens member 4 and the elastic face-abutting member 5 are fixed together and they are handled as one-bodied eye-cup 1 with a dioptrical lens. And therefore the lens member 4 and the elastic face-abutting member 5 may be advantageously re-fixed together without the troublesome separate re-fixing. The left and right eye-cups (eye-cups for respective right and left eyes) are connected with an elastic member 6 (made of elastomer).

Figure 2:
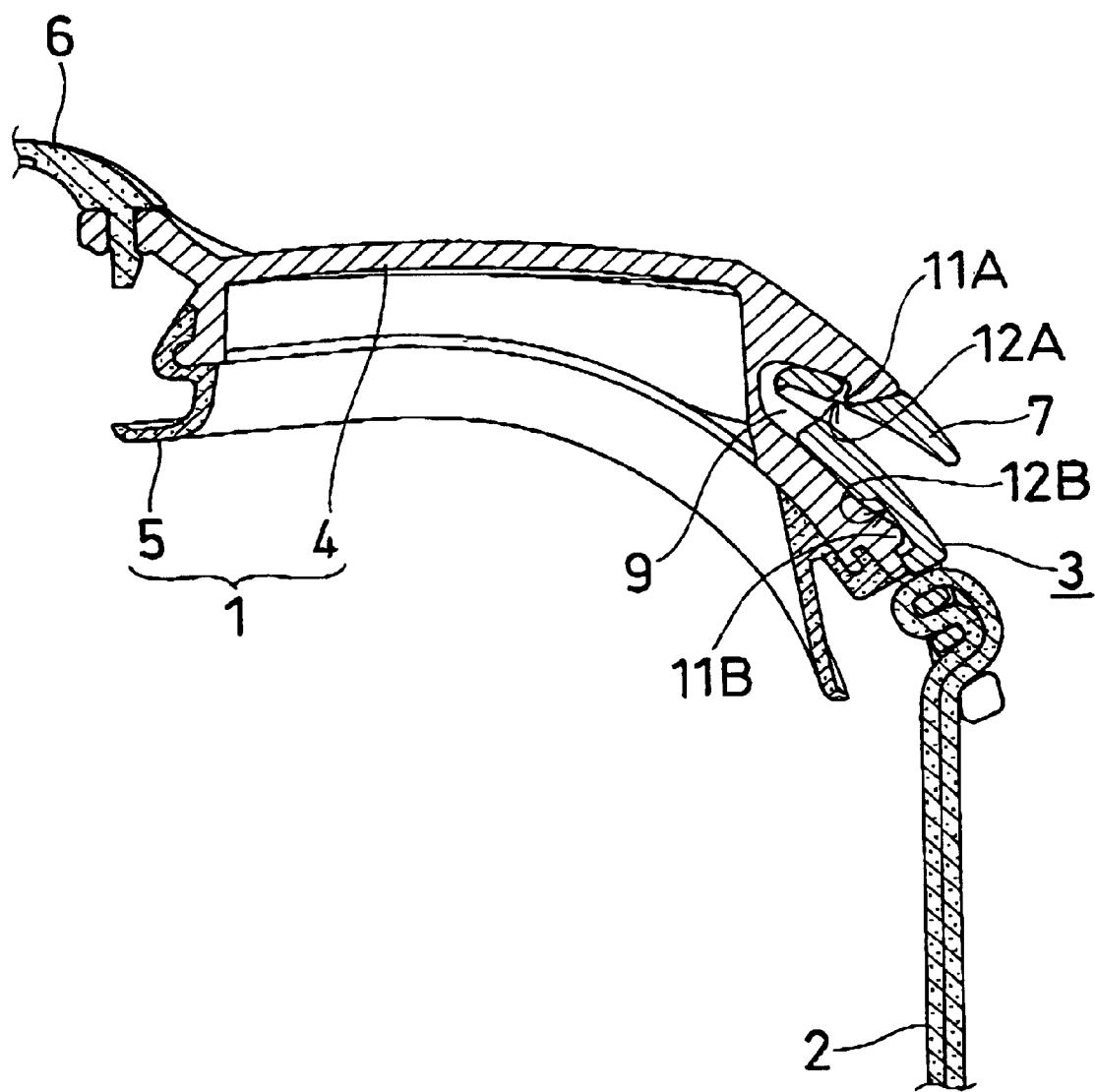
FIG. 2 is an enlarged view of the essential part of the goggles in FIG. 1.
Figure 3:
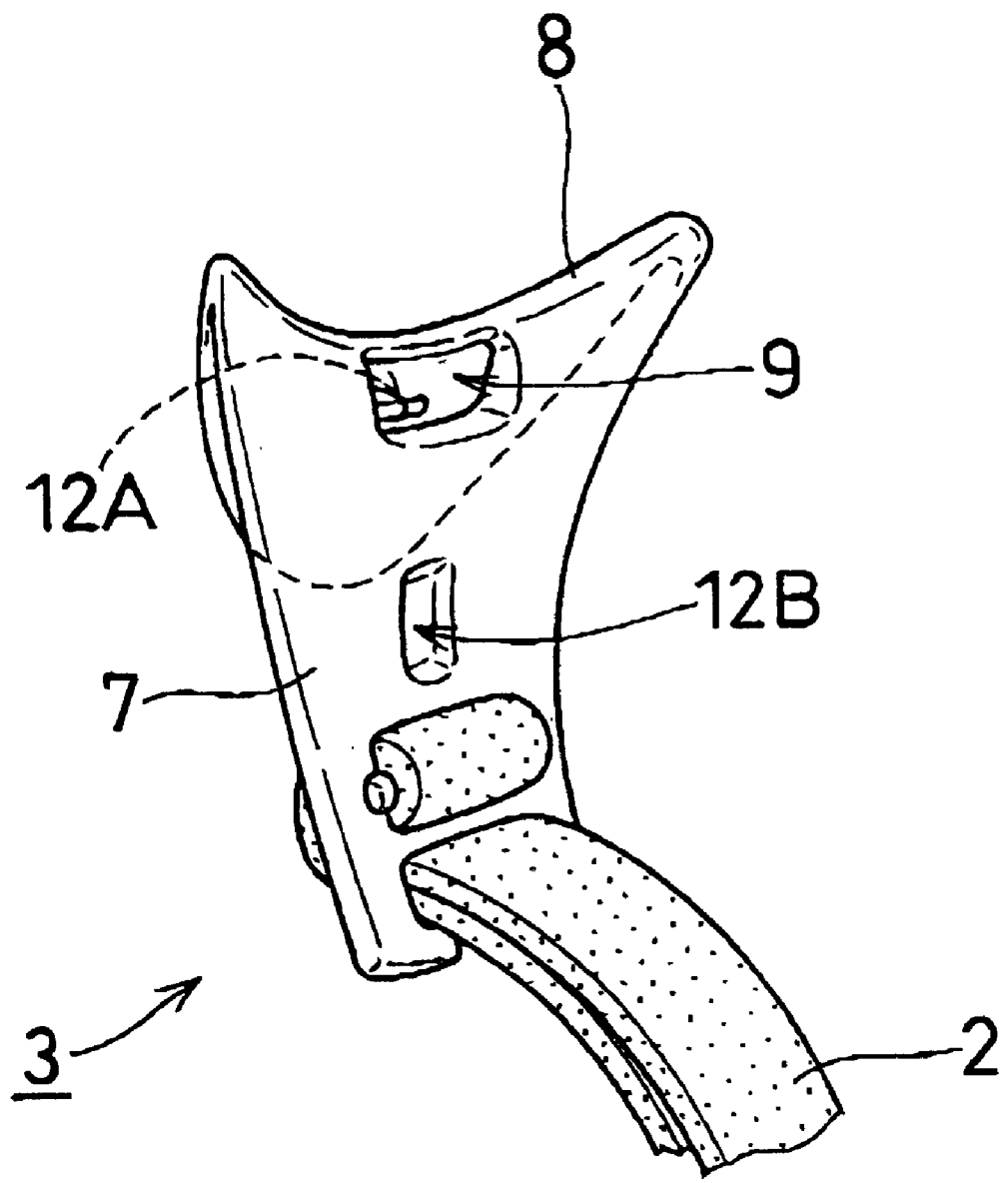
FIG. 3 is a perspective view of an elastic bent piece of a coupling member of the goggles in FIG. 1, the piece having a V-shape section.

The connecting end of the coupling member 3 of the goggles is provided with an elastic bent piece 7 that has a V-shape section and a spring property. As shown in FIGS. 2 and 3, a bent part 8 (see FIGS. 3 and 5) of the elastic bent piece 7 with a V-shape section is provided with a cut 9 in an oblong aperture shape for adjusting the strength of the spring property. When the length of the cut 9 is made longer, the spring property becomes more resilient, while the length of the cut 9 is made shorter, the spring property may be stiffer The surrounding area of the cut 9 of the oblong aperture shape is continued in a loop fashion and this enhances anti-breakage against harsh repetitious use.

Figure 5:
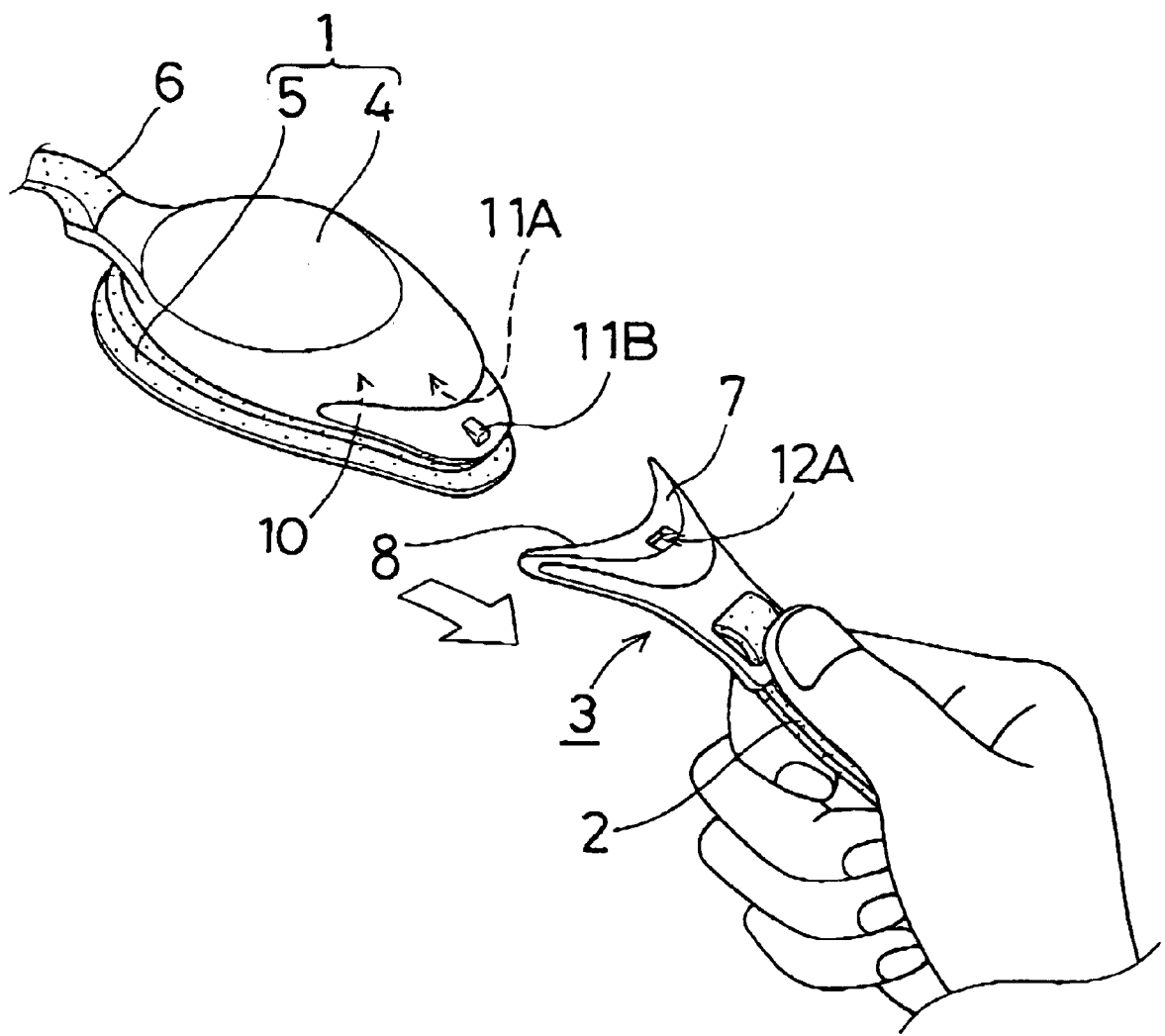
FIG. 5 is a perspective view showing the state the goggles in FIG. 1 wherein the eye-cup and the coupling member are separated away.
Figure 6:
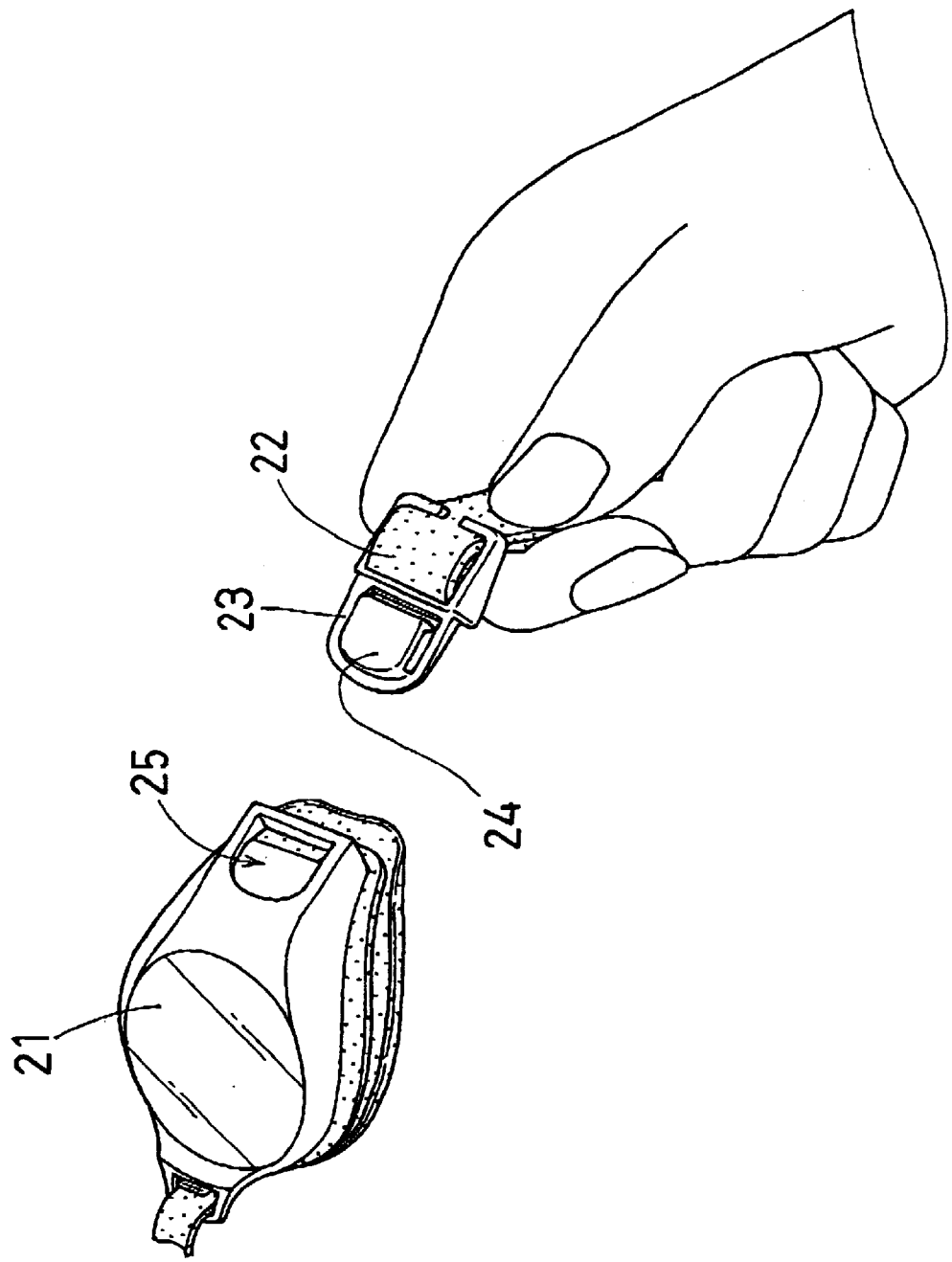
FIG. 6 is a perspective view to explain how to use conventional goggles.

The eye-cup has a connection recess 10, as shown in FIG. 5. The elastic bent piece 7 of the connecting member 3 and the connection recess 10 of the eye-cut are engagingly fixed with each other. The upper and lower faces of the connection recess 10 on the eye-cup 1 are provided with respective engaging protrusions 11A, and 11B. And the elastic bent piece 7 of the coupling member 3, the piece 7 being with a V-shape section, are provided with respective engaging dents 12A and 12b at positions corresponding to the engaging protrusions 11A and 11B. Alternatively, the connection recess 10 on the eye-cup 1 may have engaging dents, instead of the protrusions 11A and 11B, while the elastic bent piece 7 may have protrusions, instead of the engaging dents 12A and 12B (not shown).

The engaging protrusion 11A formed on the upper face of the connection recess 10 on the eye-cup 1 and the associated engaging dent 12A of the elastic bent piece 7 are formed oblong transversely with the separation direction of the coupling member 3. This ensures the engagement between the eye-cup 1 and the coupling member 3 and prevents an unwanted release contrary to a wearer's intension.

On the other hand the engaging protrusion 11B formed on the lower face of the connection recess 10 of the eye-cup 1 and the associate engaging dent 12B of the elastic bent piece 7 are formed oblong along with separation directions of the coupling members 3. This prevents the displacement between the eye-cup 1 and the coupling member 3 and mutual rotating movement therebetween.

Only either of the engaging protrusions 11A and 11B and the engaging dents 12A and 12B may be formed either on the upper or lower face (not shown in the drawings). For example, the engaging protrusion 11B formed on the lower face of the connection recess 10 of the eye-cup 1 and the associated engaging dent 12B of the elastic bent piece 7 may be formed oblong along with the separation directions of the coupling member 3 so that the engagement between the eye-cup 1 and the coupling member 3 are secured. In this case, the displacement and rotating movement between the eye-cup 1 and the coupling members 3 will be subsequently prevented.

With the construction stated above, the engaging protrusions 11A and 11B of the eye-cup 1 and the engaging dents 12A and 12B of the coupling member 3 are hooked together to be fitted in an engagement state. And as shown in FIGS. 4 and 5, when removing the eye-cup 1 from the coupling member 3, the gap in the V-shape is narrowed to release the hooked engagement between the engaging protrusions 11A and 11B and the engaging dents 12A and 12B, and then the engagement is released.

In the goggles of the present invention, the elastic bent piece 7 of the coupling member 3, the piece being with a V-shape section and a spring property, and the connection recess 10 of the eye-cup 1 are engagingly fixed together. By narrowing the gap in the V-shape of the elastic bent piece 7, the engagement therebetween are released.

Figure 4:
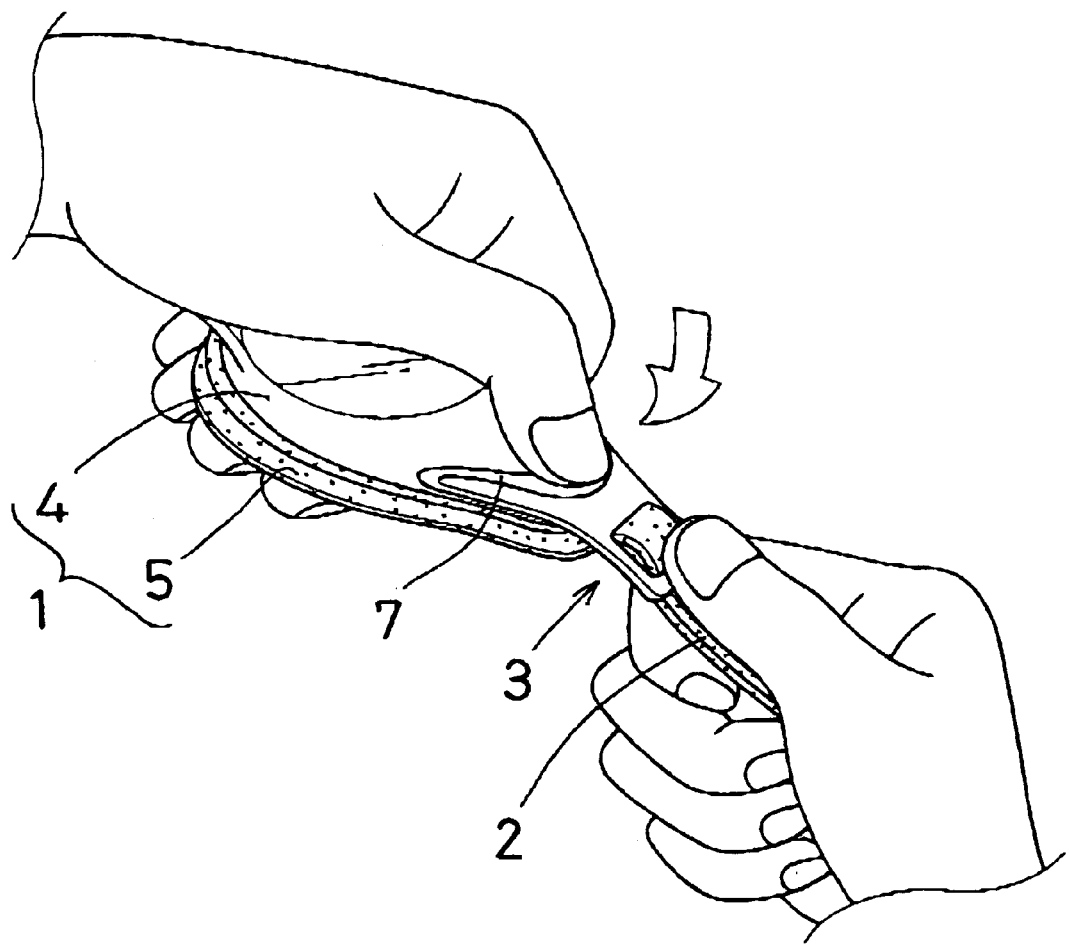
FIG. 4 is a perspective view showing the state the eye-cup and the coupling member of the goggles in FIG. 1 are about to be released.

As shown in FIG. 4, when separating the eye-cup 1 and the coupling member 3, the elastic bent piece 7 of the coupling member 3, the piece 7 being with a V-shape section and a spring property, is pressed down to narrow the gap in the V-shape, then the hooked state between the engaging protrusions 11A and 11B and the engaging dents 12A and 12B is released, and consequently the disengagement between them is obtained. And as shown in FIG. 5, in this state, at least one of the respective members are shifted in the separation direction and the members are easily separated away from each other.

Namely, as in the state wherein the elastic bent piece 7 is being pressed down, the piece 7 is shifted in the separation direction so that the mutual separation can be obtained. And with such an easy manipulation, the eye-cup and the coupling member 3 may be more advantageously and easily separated compared with in conventional goggles.

When coupling them together, only pushing the coupling member 3 in the connection recess 10 of the eye-cup 1 to the extent where the engaging protrusions 11A and 11B become to hook on the engaging dents 12A and 12B will lead to a mutual engagement. This manipulation is also easy and reliable. Therefore, in the goggles of the present invention, easy and reliable engagement and disengagement between the members can be advantageously achieved compared with in conventional ones.

Furthermore, if the push-in portion of the elastic bent piece 7 with a V-shape section is made larger, the manipulating area becomes larger, and the pushing manipulation with the fingers of a wearer becomes easier. This is a further advantage of the present invention.

With the construction stated above, the present invention provides goggles wherein the eye-cup and the coupling member can be easily coupled together and separated away from each other compared with conventional goggles due to the feature in which the mutual engagement can be released by simply narrowing the gap distance in the V-shape of the elastic bent piece of the coupling member.

What is claimed is:

1. Goggles with an eye-cup and a belt member coupled with a coupling member, comprising:

an elastic bent piece provided on an eye-cup-side end of said coupling member, said elastic bent piece being bent back toward a belt-member-side end thereof to form a V-shape section mad provide a spring property;

a connection recess for receiving said V-sped elastic bent piece being provided on said eye-cup; and wherein said elastic bent piece and said connection recess are fixed in a mutually engaging state, a said engaging state is released by narrowing a gap distance in the V-shape of said elastic bent piece.

2. Goggles according to claim 1, farther comprising a cut being formed on a bent part of said elastic bent piece with the V-shape section, said cut being for adjusting a strength of the spring property.

3. Goggles according to claim 2, wherein said cut formed on said bent part are made in an oblong aperture.

4. Goggles according to claim 1, further comprising an engaging protrusion and an associated engaging dent which put said elastic bent piece and said connection recess in a mutual engaging state.

5. Goggles according to claim 4, wherein said engaging protrusion and said associated engaging dent are formed to prevent an unwanted separation between said eye-cup and said coupling member contrary to a wearer's intention.

6. Goggles according to claim 4, wherein said engaging protrusion and said associated engaging dent are formed to prevent displacement and mutual rotating movement between said eye-cup and said coupling member.

7. Goggles according to claim 1, wherein said eye-cup includes a lens member and an elastic face-abutting member, and said lens member and said elastic face-abutting member are integrally fixed together.

\* \* \* \* \*